US012788479B2

(12) United States Patent
Paz et al.

(10) Patent No.: US 12,788,479 B2
(45) Date of Patent: Nov. 10, 2026

(54) TISSUE ABLATION GUIDED BY ELECTRICAL IMPEDANCE SPECTROSCOPY

(71) Applicant: FOCAL MEDICAL TECHNOLOGY LTD, Or Yehuda (IL)

(72) Inventors: Adrian Paz, Petah Tikva (IL); Nadav Ben Daat, Kibbutz Lehavot Haviva (IL); Benny Gamus, Ramat Gan (ID)

( * ) Notice: Subject to any disclaimer, the term of this patent is extended or adjusted under 35 U.S.C. 154(b) by 261 days.

(21) Appl. No.: 18/688,800

(22) PCT Filed: Sep. 12, 2022

(86) PCT No.: PCT/IL2022/050987
§ 371 (c)(1),
(2) Date: Mar. 4, 2024

(87) PCT Pub. No.: WO2023/042196
PCT Pub. Date: Mar. 23, 2023

(65) Prior Publication Data
US 2024/0366290 A1 Nov. 7, 2024

Related U.S. Application Data

(60) Provisional application No. 63/244,292, filed on Sep. 15, 2021.

(51) Int. Cl.

| | |
|---|---|
| ***A61B 18/14*** | (2006.01) |
| ***A61B 18/00*** | (2006.01) |
| ***A61B 34/10*** | (2016.01) |
| ***G16H 50/30*** | (2018.01) |

(52) U.S. Cl.
CPC .......... *A61B 18/1477* (2013.01); *A61B 34/10* (2016.02); *G16H 50/30* (2018.01);
(Continued)

(58) Field of Classification Search
CPC ................ A61B 18/1477; A61B 18/18; A61B 2018/00547; A61B 2018/00577;
(Continued)

(56) References Cited

U.S. PATENT DOCUMENTS 6,120,493 A * 9/2000 Hofmann .............. A61N 1/327
607/148
8,361,066 B2 1/2013 Long et al.
(Continued)

FOREIGN PATENT DOCUMENTS

CA 3228131 A1 3/2023
CN 105616004 A 6/2016
(Continued)

*Primary Examiner* — Ronald Hupczey, Jr.

(57) ABSTRACT

A system and method use impedance, optionally in combination with one or more imaging techniques (e.g., US, CT, MRI, PET scan, SPECT, fluoroscopy, endoscopy) to discern between diseased and healthy tissue, and/or to determine location, size, boundaries and/or multifocal foci of diseased tissue. Impedance is measured between groups of electrodes. The electrodes may be inserted with a plurality of interstitial probes positionable within tissue (e.g., prostate). One or more electrodes may be mounted on each probe. An algorithm (e.g., machine learning capable) may discern diseased tissue and/or compile a histological map of the tissue. The same system optionally delivers ablative energy, or electroporation and/or electrochemotherapy to identified diseased (or high risk) tissue as a treatment modality. Mapping, treatment on the mapping and/or post-treatment scanning may be performed via the same device. The multi-use system may reduce navigating of the tissue to deliver focal treatment to tumor foci.

11 Claims, 6 Drawing Sheets

(52) U.S. Cl.
CPC ................. *A61B 2018/0016* (2013.01); *A61B 2018/00547* (2013.01); *A61B 2018/00577* (2013.01); *A61B 2018/00613* (2013.01); *A61B 2018/00642* (2013.01); *A61B 2018/00732* (2013.01); *A61B 2018/00875* (2013.01); *A61B 2034/104* (2016.02)

(58) Field of Classification Search
CPC ........... A61B 2018/00613; A61B 2018/00642; A61B 2018/00702; A61B 2018/00726; A61B 2018/00732; A61B 2018/00738; A61B 2018/00875; A61B 2018/124; A61B 2018/143; A61B 2018/2005; A61B 34/10; A61N 1/327; A61N 5/1027
See application file for complete search history.

(56) References Cited

U.S. PATENT DOCUMENTS

| | | | | |
|---|---|---|---|---|
| 8,548,562 | B2 | 10/2013 | Trachtenberg et al. | |
| 9,877,788 | B2 | 1/2018 | Stoianovici et al. | |
| 10,238,447 | B2 | 3/2019 | Neal, II et al. | |
| 10,575,899 | B2 | 3/2020 | Fruland et al. | |
| 11,745,027 | B2 | 9/2023 | Stoianovici et al. | |
| 12,214,189 | B2 | 2/2025 | Lorenzo et al. | |
| 2018/0235694 | A1 | 8/2018 | Rusin et al. | |
| 2019/0083172 | A1 | 3/2019 | Ladtkow et al. | |
| 2019/0099214 | A1 | 4/2019 | Rubinsky et al. | |
| 2019/0336757 | A1 * | 11/2019 | Rodriguez | A61N 1/0412 |

FOREIGN PATENT DOCUMENTS

| | | | | |
|---|---|---|---|---|
| CN | 117940083 | A | 4/2024 | |
| EP | 4401661 | A4 | 8/2025 | |
| JP | 2020520717 | A | 7/2020 | |
| RO | 129697 | A2 | 8/2014 | |
| WO | 03026525 | A1 | 4/2003 | |
| WO | WO-2009036471 | A1 * | 3/2009 | A61B 18/1492 |
| WO | 2023042196 | A1 | 3/2023 | |

* cited by examiner

TISSUE ABLATION GUIDED BY ELECTRICAL IMPEDANCE SPECTROSCOPY

RELATED APPLICATION/S

This application claims the benefit of priority under 35 USC § 119(e) of U.S. Provisional Patent Application No. 63/244,292 filed 15 Sep. 2021, the contents of which are incorporated herein by reference in their entirety.

FIELD AND BACKGROUND OF THE INVENTION

The present invention, in some embodiments thereof, relates to a system and method for evaluating tumors and providing reliable focused treatment of the tumor (e.g., focal therapy), more particularly, but not exclusively, without massive damage to the surrounding tissue.

Currently, there is lacking a reliable way to evaluate of tumors of the prostate, e.g., mapping tumors to determine their precise position and size and/or evaluating their state. Additionally, there is lacking reliable focused treatment for such tumors, e.g., which destroy tumor tissue without massive damage to the prostate.

U.S. Pat. No. 8,548,562 appears to disclose, an imaging and diagnostic system and method to differentiate between malignant and non-malignant tissue of a prostate and surrounding region, wherein the system acquires imaging data from the prostate and surrounding proximal region, and processes the data to differentiate areas of tissue malignancy from non-malignant tissue. A sectioning device or ablative device is provided, wherein the ablative device is operable by automation for receiving the imaging output coordinates and defining the trajectory and quantity of energy or power to be delivered into the malignant tissue. A control system determines calculated energy or power to be deposited into the malignant tissue during ablation, to minimize destruction of the non-malignant tissue within the prostate and surrounding tissue. The system operates on generated ablative device output data.

Additional background art includes Japanese Utility Application No. 2020520717, U.S. Pat. Nos. 9,877,788, 10,575,899, Romanian Application No. 129697 and U.S. patent application No. 2020/086140 and Chinese Patent No. 105616004, U.S. Pat. No. 8,361,066, U.S. patent application No. 2019/099214 and Collettini, et al., "Image-guided Irreversible Electroporation of Localized Prostate Cancer: Functional and Oncologic Outcomes", Radiology 2019 292: 1, 250-257.

Therefore, there is still a need for a system and a method for evaluating tumors and providing reliable focused treatment thereof without causing massive damage to the surrounding tissue.

SUMMARY OF THE INVENTION

According to an aspect of some embodiments of the invention, there is provided a method of diagnosis including; positioning a plurality of electrodes in tissue of interest; passing signals between different groups of the plurality of electrodes; recording an effect of location of electrodes on the signals; and mapping a property of the tissue based on the effect of location of the electrodes on the signals.

According to some embodiments of the invention, the passing includes of an electric signal.

According to some embodiments of the invention, the passing includes of an alternating electric signal.

According to some embodiments of the invention, the tissue includes a prostate.

According to some embodiments of the invention, the plurality of electrodes are mounted on a plurality of probes and the probes are inserted until the electrodes reach the target tissue.

According to some embodiments of the invention, one or more of the plurality of probes is inserted percutaneously.

According to some embodiments of the invention, one or more of the plurality of probes is inserted trans-perennially.

According to some embodiments of the invention, one or more of the plurality of probes includes a plurality of electrodes.

According to some embodiments of the invention, recording the effect includes recording a time dependent change in the property resulting from the passing the signal.

According to some embodiments of the invention, the recording includes recording an impedance.

According to some embodiments of the invention, the signal, is delivered sequentially, each time between at least 2 electrodes, adjacent to one of a plurality of high-risk locations.

According to some embodiments of the invention, the signal includes ablative radiofrequency energy, or electroporation.

According to some embodiments of the invention, the method where the signal is delivered sequentially, each time between at least 2 electrodes, adjacent to one of a plurality of high-risk locations.

According to some embodiments of the invention, the signal includes ablative energy delivered in pulses between at least 2 electrodes, and wherein paths of the pulses are intersecting at a particular location.

According to some embodiments of the invention, a plurality of frequencies are delivered concomitantly using a special wave pattern.

According to an aspect of some embodiments of the invention, there is provided a method of treatment including; positioning a plurality of electrodes in a tissue of interest; passing signals between different groups of the plurality of electrodes; and triggering destruction of diseased tissue by the passing, thereby providing a therapeutic effect.

According to some embodiments of the invention, the signals includes alternating electric current.

According to some embodiments of the invention, the destruction is by radiofrequency ablation.

According to some embodiments of the invention, the destruction is by electroporation.

According to some embodiments of the invention, the destruction is by chemo-electroporation or calcium electroporation.

According to some embodiments of the invention, the method further includes: passing alternating the signals between different groups of the plurality of electrodes; recording an effect of location on the signals; and mapping a property of the tissue based on the effect of location.

According to some embodiments of the invention, electrical ablation is delivered in pulses.

According to some embodiments of the invention, electrical ablation is induced by tissue heating.

According to some embodiments of the invention, electrical ablation is induced by electroporation.

According to some embodiments of the invention, electroporation is delivered in pulses.

According to some embodiments of the invention, the electroporation is used in conjunction with one or more chemotherapeutic compounds.

According to some embodiments of the invention, the electroporation used in conjunction with one or more chemotherapeutic compounds is synergistic.

According to some embodiments of the invention, the passing is selected from the group including: focused ablation, electroporation, electrochemical or chemo-electroporation between local pairs of electrodes.

According to some embodiments of the invention, the mapping is performed before the triggering.

According to some embodiments of the invention, the mapping is performed concurrently with the triggering.

According to some embodiments of the invention, the mapping is performed after the triggering.

According to some embodiments of the invention, the mapping and the triggering are concurrent and the triggering is adjusted based on the mapping.

According to some embodiments of the invention, the destruction of tissue is less than ⅕ of a volume of the tissue.

According to some embodiments of the invention, the destruction is delivered to locations with high risk of disease.

According to some embodiments of the invention, the therapeutic effect is delivered interstitially at a location of an interstitial probe.

According to some embodiments of the invention, the therapeutic effect is selected from a group including: contact radiofrequency energy, non-contact radiofrequency energy, electroporation, ultrasonic energy, laser energy, gamma radiation, beta radiation, alpha radiation, immunotherapy, or a combination thereof.

According to an aspect of some embodiments of the invention, there is provided a system including: a plurality of electrodes; a plurality of interstitial probes configured for positioning the plurality of electrodes within a volume of tissue; each of the plurality of probes provided with at least one of the plurality of electrodes and at least one of the of plurality of probes including a plurality of the electrodes; and a control unit in communication with the probes, the control unit programmed to: deliver signals at a plurality of frequencies between various groups of the plurality of electrodes; and calculate a characteristic of an interaction between the signals and the tissue at the plurality of frequencies and at a plurality of locations.

According to some embodiments of the invention, the signals includes at least one of non-ablative electrical current and ablative electrical current.

According to some embodiments of the invention, the control unit is automated.

According to some embodiments of the invention, the control unit is configured to determine a location of at least 2 of the plurality of probes.

According to some embodiments of the invention, the control unit is configured to control positioning of the plurality of probes, plurality of electrodes, or both.

According to some embodiments of the invention, the plurality of probes are introduced into the volume of tissue in mostly parallel directions.

According to some embodiments of the invention, the plurality of probes is inserted trans-perennially.

According to some embodiments of the invention, the volume of tissue is part of or an entire prostate gland.

According to some embodiments of the invention, the control unit is further configured to perform a comparison between the characteristics detected at each of the plurality of locations.

According to some embodiments of the invention, the control unit is further configured to reference characteristics of non-diseased and diseased tissue.

According to some embodiments of the invention, the control unit is further configured to estimate a risk of disease at each particular location from the plurality of locations, within the volume of tissue.

According to some embodiments of the invention, the control unit is programed to generate a histological map of the tissue volume depicting a risk of disease at each location.

According to some embodiments of the invention, the histological map is generated using information from additional imaging modalities.

According to some embodiments of the invention, the additional imaging modalities are selected from the group including: ultrasound, computed tomography (CT), Magnetic resonance imaging (MRI), positron emission tomography (PET) scan, single-photon emission computerized tomography (SPECT) scan, fluoroscopy, endoscopy, laparoscopy, or any combination or fusion of modalities.

According to some embodiments of the invention, the characteristic is an impedance.

According to some embodiments of the invention, reaction of the tissue to ablating energy is used for diagnostic purposes.

According to an aspect of some embodiments of the invention, there is provided a system including: a plurality of electrodes; a plurality of interstitial probes configured for positioning the plurality of electrodes within a volume of tissue; each of the plurality of probes provided with at least one of the plurality of electrodes and at least one of the of plurality of probes including a plurality of the electrodes; and a control unit in communication with the probes, the control unit programmed to: deliver electrical energy in between groups of the plurality of electrodes to ablate tissue at locations showing high risk of disease, wherein paths are intersecting at a particular location causing a therapeutic effect at their intersection and having lesser effect elsewhere.

According to some embodiments of the invention, the control unit is further programmed to deliver electrical energy in pulses.

According to some embodiments of the invention, control unit is further programmed to deliver the therapeutic effect as a result of focused ablation, electroporation, electrochemical or chemo-electroporation between local pairs of electrodes.

According to some embodiments of the invention, control unit is further programmed to deliver the therapeutic effect to the locations with high risk of disease.

According to some embodiments of the invention, control unit is further programmed to deliver the therapeutic effect interstitially at the location of the interstitial probes.

According to some embodiments of the invention, control unit is further programmed to deliver the therapeutic effect selected from a group including: contact radiofrequency energy, non-contact radiofrequency energy, electroporation, ultrasonic energy, laser energy, gamma radiation, beta radiation, alpha radiation, immunotherapy, or a combination thereof.

According to some embodiments of the invention, control unit is further programmed to deliver the therapeutic effect to less than ⅕ of the volume of tissue.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DESCRIPTION OF SPECIFIC EMBODIMENTS

Figure 1:
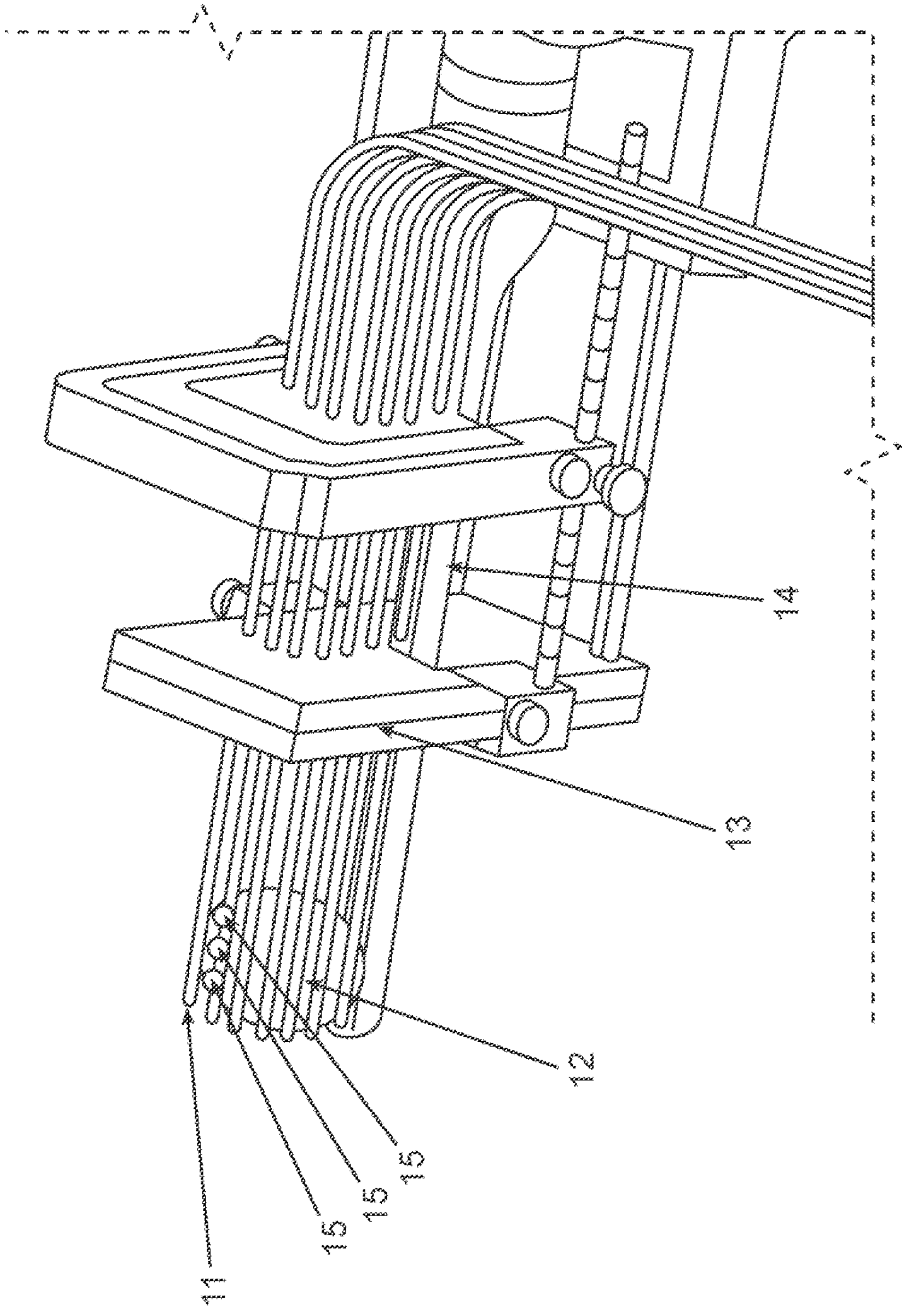
FIG. 1 is an exemplary photograph of a system comprising a plurality of electrodes in accordance with some embodiments of the current invention.

The present invention, in some embodiments thereof, relates to a system and method for evaluating tumors and providing reliable focused treatment thereof, more particularly, but not exclusively, without massive damage to the surrounding tissue.

Overview

The present invention, in some embodiments thereof, relates to a system and method for evaluating tumors and providing reliable focused treatment thereof, more particularly, but not exclusively, reducing damage to the surrounding tissue.

According to some embodiments, a system is disclosed comprising: a plurality of interstitial probes positionable within a volume of tissue, each probe may be provided with 2 or more electrodes, and/or a control unit in communication with the probes.

According to some embodiments, a system is disclosed including a plurality of electrodes, a plurality of interstitial probes which may be configured for positioning said plurality of electrodes within a volume of tissue, wherein each of the probes may be provided with at least one of said plurality of electrodes, and/or a control unit in communication with the probes.

According to some embodiments, the control unit may be configured to determine the location of at least 2 probes and/or electrodes. Optionally, the control unit may be configured to control positioning of the plurality of probes, plurality of electrodes, or both. Optionally, the plurality of probes may be introduced into the volume of tissue in mostly parallel directions. Optionally, the plurality of probes may be inserted into a volume of tissue trans-perennially. Optionally, the tissue may be part of or the entire prostate gland.

According to some embodiments, the control unit may be programmed to deliver energy (e.g., electrical current at any of plurality of frequencies for example radiofrequency (RF)) between various groups of the plurality of electrodes. Optionally, the energy may be non-ablative and/or ablative electrical current. The energy may be low current (e.g., a few milli-Amperes for example for imaging/mapping bioimpedance) and/or at higher currents (e.g., for testing tissue sensitivity and/or recovery and/or for ablation of diseased tissue). Optionally, a plurality of energy signals may be pass between various groups of the plurality of electrodes. Optionally, the energy may pass between various groups of the plurality of electrodes sequentially and/or simultaneously. Optionally, the plurality of energy may pass between various groups of the plurality of electrodes in pulses. Optionally, the reaction of the tissue to energy may be measured and/or may be used for diagnostic purposes. Optionally, the reaction of the tissue to energy may be measured for diagnosis and/or to evaluate the progress of treatment.

According to some embodiments, the control unit may be programmed to calculate a characteristic of the interaction between the signal and the tissue at the plurality of frequencies and at a plurality of locations. Optionally, the characteristic may include an impedance characteristic. The measured characteristics of the tissue, for example including bioimpedance, may be used to improve the ablation protocol (frequency, power, etc.) and/or focalized treatment (i.e., to reduce influence on surrounding tissue).

According to some embodiments, the control unit may be programmed to detect and/or calculate impedance characteristics at one or the plurality of frequencies at a plurality of locations. According to some embodiments, the control unit may be programmed to perform a comparison between the found impedance characteristics at each location and/or reference characteristics of non-diseased and diseased tissue. According to some embodiments, the control unit may be programmed to estimate the risk of disease at each particular location from the plurality of locations, within the volume of tissue. Optionally, the bioimpedance measurements, may be done in 2- 3- or 4-polar configuration. In the tetrapolar method, the current may be applied between one set of electrodes while voltage may be measured by a close-by pair.

According to some embodiments, the control unit may be programmed to deliver ablative energy such as: radiofrequency current or electroporation. According to some embodiments, the control unit may be programmed to deliver ablative energy in bipolar and/or multipolar mode between 2 or more of the electrodes to ablate tissue at locations showing high risk of disease.

According to some embodiments, the control unit may be automated.

According to some embodiments, the impedance characteristic may include one or more of: impedance magnitude, impedance phase, etc. Optionally, the real and imaginary (resistive and reactive) components of impedance may be considered separately.

According to some embodiments, the estimated risk of disease may be based on a difference between a detected impedance characteristic value at a location and reference values and/or a comparison between various locations and/or a comparison to reference values. Optionally, statistical calculations may be used to determine the significance of determinations and/or the probability of various disease and/or healthy tissue types. According to some embodiments, a comparison may be performed between the detected characteristic at each location and reference characteristics of non-diseased and diseased tissue.

According to some embodiments, a map such as a tridimensional map, may be generated of the tissue volume depicting the estimated risk of disease at each location.

According to some embodiments, the map of risk of disease may be fused with an imaging map of the tissue using information from additional imaging modalities. Optionally, combining techniques may provide a more accurate histological map of the tissue. For example, the additional imaging modalities may include: ultrasound, computed tomography (CT), Magnetic resonance imaging (MRI), positron emission tomography (PET) scan, single-photon emission computerized tomography (SPECT) scan, fluoroscopy, endoscopy, laparoscopy, or any combination or fusion of modalities.

According to some embodiments, an impedance map may be fused with previous imaging map of ultrasound, computed tomography (CT), Magnetic resonance imaging (MRI), positron emission tomography (PET) scan, single-photon emission computerized tomography (SPECT) scan, fluoroscopy, endoscopy, laparoscopy, or any combination or fusion of modalities.

According to some embodiments, an impedance map may be fused with concomitant imaging map of ultrasound, computed tomography (CT), Magnetic resonance imaging (MRI), positron emission tomography (PET) scan, single-photon emission computerized tomography (SPECT) scan, fluoroscopy, endoscopy, laparoscopy, or any combination or fusion of modalities. Various data may optionally be fused live on an output device (e.g., a computer screen of physician). In some embodiments, fusing various kinds of data together may make it easier to recognize issues and/or make treatment decisions.

According to some embodiments, a risk of disease of each voxel may be calculated and/or estimated based on the impedance data and on from previous and/or concomitant imaging modalities such as: ultrasound, computed tomography (CT), Magnetic resonance imaging (MRI), positron emission tomography (PET) scan, single-photon emission computerized tomography (SPECT) scan, fluoroscopy, endoscopy, laparoscopy, or any combination or fusion of modalities.

According to some embodiments, an additional interstitial imaging modality such as optical coherence tomography, may be used in conjunction with impedance data to calculate the risk of disease of some or all the voxels.

According to some embodiments, a risk of disease of each voxel from these multiple data sets may be estimated using advanced algorithms such as machine learning and/or neural networks and/or deep learning. Optionally, training of such AI algorithms may be using them in comparation with detailed 3D tumor or disease histological mapping of tissue. Optionally, such algorithms may improve continuously with additional data.

According to some embodiments, additional patient clinical, serologic and genetic and proteomic data may be used to improve accuracy.

According to some embodiments, the system may be used to evaluate tumors within a tissue.

According to some embodiments, the system for evaluating tumors within a tissue may include a 3D array of electrodes which may be introduced into the tissue (e.g., prostate) and used for 3D tomography (e.g., impedance tomography). Optionally, the electrodes may be inserted into the tissue in a plurality of locations. Optionally, the electrodes may be located on a plurality of probes. Optionally, each or the plurality of probes may have a plurality of electrodes. Optionally, the electrodes may be used to measure an impedance characteristic. Optionally, the impedance characteristic may be mapped for example using 3D tomography. Optionally, electrical characteristics (e.g., impedance) may be measured and/or mapped for signals of various frequencies (e.g., using spectroscopic techniques). Optionally, the current may be non-destructive. Optionally, the non-destructive (e.g., non-ablative) current is delivered between 2 or more electrodes, adjacent one of the plurality of locations. Optionally, reversible electroporation may be used to test sensitivity and/or recovery of the tissue. Optionally, the spectroscopic and geometric data may be combined. Optionally, the combined data may be used to provide a 3D histological map of the tissue.

According to some embodiments, tumor tissue may be recognized based on increased sensitivity of tumor tissue to electroporation compared to benign tissue. For example, monitoring the change in tissue impedance with initiation of electroporation may assist in refining the tumor risk at each voxel. Optionally, after an initial mapping of the tissue impedance at each voxel, electroporation may be initiated between all or some pairs of nearby electrodes and/or changes in impedance may be detected and/or resulting data used to refine the determination of tumor risk at each voxel.

According to some embodiments, a method of diagnosis may include positioning a plurality of electrodes in tissue of interest, passing a signal (e.g., an electric current) between different groups of the plurality of electrodes. The signal may include for example various magnitudes, frequencies and/or waveforms. Optionally, method further includes recording an effect of location on the electrical signals and/or mapping a property of the tissue based on the effect of location on the signal. Optionally, the signal may include an electric current, for example, a radiofrequency current. Optionally, the electric current may be alternating and/or direct current.

According to some embodiments, a plurality of different signals (e.g., different frequencies, magnitudes and/or waveforms) may be delivered. Optionally, other factors may be added to the signal (e.g., adding chemicals for example for chemo-electroporation). Optionally, the plurality of signals may be delivered, sequentially, simultaneously, concomitantly, in pulses, and/or a combination thereof. Optionally, the plurality of signals may be delivered concomitantly using a complex wave pattern.

According to some embodiments, the signal may be non-ablative. Optionally, the non-ablative signal may be delivered sequentially, simultaneously and/or in pulses. Optionally, the non-ablative signal may be delivered each time between at least 2 electrodes. Optionally, the non-ablative signal may be delivered adjacent to one of a plurality of high-risk locations.

According to some embodiments, the energy (e.g., electrical current) may be ablative. Optionally, the ablative current may be delivered sequentially, simultaneously and/or in pulses. Optionally, the ablative current may be delivered each time between at least 2 electrodes. Optionally, the ablative current may be delivered adjacent to one of a plurality of high-risk locations. Optionally, the ablative energy may be delivered such that the current paths of the pulses may intersect at a particular location.

According to some embodiments, the plurality of electrodes may be mounted on a plurality of probes. Optionally, the probes may be inserted until the electrodes reach the target tissue (e.g., prostate tissue). Optionally, the one or more of the plurality of probes may be inserted transperennially.

According to some embodiments, recording the effect of location of the transmitting and/or measuring electrodes on the electrical signals. The effect may change over time which may indicate a time dependent change in a property resulting from the passing energy through a volume. Optionally, the recording may include a recording a measured impedance.

According to some embodiments, a system is disclosed including a plurality of electrodes, a plurality of interstitial probes configured for positioning the plurality of electrodes within a volume of tissue, wherein each of the probes may be provided with at least one of the plurality of electrodes and at least one of the of plurality of probes may include a plurality of the electrodes, and a control unit in communication with the probes.

According to some embodiments, the control unit may be programmed to deliver energy (e.g., radiofrequency current) between groups of the plurality of electrodes. The energy is optionally configured to ablate tissue at locations showing high risk of disease. For example, the current paths may intersect at a particular (e.g., a diseased) location causing a therapeutic effect (e.g., by causing ablation/necrosis of malignant at their intersection). Optionally, the signals may be configured to have a lesser effect at areas where signals do not intersect (e.g., at a point of contact of an electrode with the tissue). Optionally, the control unit may be further programmed to deliver energy between groups of the plurality of electrodes simultaneously, sequentially, in pulses, and/or a combination thereof According to some embodiments, the control unit may be programmed to deliver the therapeutic effect as a result of focused ablation, electroporation, electrochemical or chemo-electroporation between local pairs of electrodes. Optionally, the control unit may be programmed to deliver the effect (e.g., by ablation/necrosis) to the locations with high risk of disease. Optionally, the control unit may be programmed to deliver the therapeutic effect interstitially at the location of the interstitial probes.

Optionally, the probes may include catheters provided with longitudinal channels, and/or tubes. Optionally, a treatment modality (e.g., chemicals for chemo-electroporation) may be delivered through the probe lumen.

According to some embodiments, the control unit may be programmed to deliver the therapeutic effect selected from a group comprising: contact radiofrequency energy, non-contact radiofrequency energy, electroporation, ultrasonic energy, laser energy, gamma radiation, beta radiation, alpha radiation, immunotherapy, or a combination thereof. Optionally, the control unit may be programmed to deliver the therapeutic effect to less than about 0.5/5, less than about ⅕, less than about ⅖, or less than about ⅗ of the volume of tissue. Each possibility is a separate embodiment. Optionally, a therapeutic effect may be delivered at the locations with high risk of disease.

In some embodiments, the control unit may suggest best positioning of probes and/or electrodes; determine the position of the electrodes or probes; and/or control a robotic positioning system which places the probes autonomously.

According to some embodiments, exploratory signals (e.g., for measuring properties) therapeutic and/or ablative electrical signals may be delivered in sequential pulses between 2 or more electrodes and/or between groups of electrodes. Optionally, the current paths of the pulses may intersect at a particular location. Optionally, the pulses may have a duty cycle of between about ½ to about 1/25, or between about ⅓ to ⅕. Optionally, heating and injury to the tissue adjacent to the electrodes surface, may be inhibited and/or the energy may be delivered relatively evenly in the volume of tissue avoiding hot or cold spots.

According to some embodiments, there is disclosed a system facilitating measurement of a precise location of a tumor, and/or focused localized treatment thereof. Optionally, some electrodes may be used both in measurement and in treatment. Optionally, measurement and treatment may be carried out without moving the electrodes. Optionally, measurement may be carried out by the electrodes which may be repositioned prior to treatment. Optionally, during treatment (e.g., either while ablating and/or during breaks in treatment) the progress of the treatment may be evaluated by one or more of the measurement techniques described herein. Optionally, this may facilitate more reliable positioning of the electrodes and/or reposition of the electrodes. Optionally, this may facilitate more accurate treatment. For example, electrode positions and/or waveform may be adjusted during treatment. Optionally, frequency, duty cycle, intensity, electrode position, current intersection, pulse time and/or duration, number of electrodes, etc. and/or a combination thereof may be adjusted.

According to some embodiments, a method for treatment is described comprising a plurality of electrodes in a tissue of interest, a plurality of interstitial probes configured for positioning the plurality of electrodes within a volume of tissue, passing alternating electric current between different groups of the plurality of electrodes, and triggering destruction of diseased tissue by the passing, thereby providing a therapeutic effect.

According to some embodiments, the passing may be selected from the group including: focused ablation, electroporation, electrochemical or chemo-electroporation between local pairs of electrodes, and/or local groups of electrodes.

According to some embodiments, the therapeutic effect may be delivered to the locations with high risk of disease. Optionally, the therapeutic effect may be delivered interstitially at the location of the interstitial probes. Optionally, the therapeutic effect may be selected from a group including: contact radiofrequency energy, non-contact radiofrequency energy, electroporation, ultrasonic energy, laser energy, gamma radiation, beta radiation, alpha radiation, immunotherapy, and/or a combination thereof.

According to some embodiments, electrical ablation may induce electroporation. Optionally, electroporation may be delivered in pulses. Optionally, electroporation may be used in conjunction with one or more chemotherapeutic compounds.

The electroporation regimen may for example but not exclusively be monopolar, bipolar or a combination thereof. The electroporation pulses may be of 100 ns to 10 ms, or particularly between 100 ns to 100 microsec, and may be of various repetition frequency. The pulses may be monophasic or biphasic and in last case symmetric or asymmetric. The pulses may be single pulses or delivered as train of pulses. The current intensity may be between 1 amp to 100 Amp and particularly between 10 Amp and 50 Amp. The voltage gradient may be between 300 V/cm to 7000 V/cm and particularly between 500 to 3000 V/cm. The number of pulse trains may be between one to 200 trains and particularly between 30 to 200 trains. The trains may be every 100 ms to every 20 s.

Optionally, the electroporation used in conjunction with one or more chemotherapeutic compounds may be synergistic. Optionally, the chemotherapeutic may be an anti-cancer compound. Optionally, the anti-cancer compound may be a small molecule, a biological molecule such as an antibody, a metal, an organometallic compound and/or a radio isotope. Such compound may be calcium ions, natrium ions, bleomycin, cisplatin, which induce cell apoptosis following the electroporation.

According to some embodiments, electrical ablation may be delivered consistently and/or in pulses. Optionally, electrical ablation may induce tissue heating. Optionally, electrical ablation in pulses may reduce the damage to the surrounding, non-diseased tissue. Optionally, the destruction of tissue may be less than about 0.5/5, less than about ⅕, less than about ⅖, or less than about ⅗ of the volume of tissue.

According to some embodiments, the method may include passing alternating electric current between different groups of the plurality of electrodes, recording an effect of location on the electrical signals, and/or mapping a property of the tissue based on the effect of location on the electrical signal. Optionally, mapping may be performed before, during and/or after the treatment. Optionally, the treatment may be adjusted during the procedure based on the mapping.

According to some embodiments, the system and/or method may be controlled by a control unit. Optionally, the control unit may be automated. Optionally, evaluation of the tumor, e.g., position, histological mapping, etc. may be automated. Optionally, a machine learning algorithm may be used to determine high risk tissue. Optionally, treatment of the tumor may be automated e.g., the treatment selected, the optimal position of a plurality of probes, the optimal position of a plurality of electrodes, the frequency to be used, the pulse duration and or rate, duty cycle, chemotherapeutic, etc. Optionally, the automated system may control variation of signals delivered, sequential, simultaneous, concomitant, in pulsed, and/or a combination thereof. Optionally, the plurality of signals may be delivered concomitantly using a complex wave pattern between pairs of electrodes and/or groups of electrodes.

In some embodiments a system may run in one of two or both of two modes:

Non-ablative, for imaging/sensing/mapping/screening. For example, the non-ablative signals may include electrical currents and/or pulses at various frequencies and/or impedance measurement. Optionally, sensing is at relatively low current and/or energy.

Ablative, for treatment of diseased (e.g., cancerous) tissue. This can be done using Radiofrequency (RF) ablation—in which the cells are ablated by the heat generated from the (alternating) current; and/or Electroporation-which creates holes in the cells, that kill them and/or other methodologies for example as disclosed herein.

EXEMPLARY EMBODIMENTS

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

According to some embodiments, a system is described comprising: a plurality of interstitial probes positionable within a volume of tissue, each one provided with 2 or more electrodes operable to treat the tissue; and a control unit in communication with the probes, the control unit programmed to: deliver non-ablative electrical current at a plurality of frequencies in bipolar or multipolar mode between two or more electrodes sequentially; calculate impedance characteristics at the plurality of frequencies at a plurality of locations; perform a comparison between the detected impedance characteristics at each location and/or between the measured value and a reference characteristics of non-diseased and diseased tissue; a comparison between the measured value at different locations; determine the risk of disease at each particular location from the plurality of locations, within the volume of tissue.

According to some embodiments, a system is described comprising: a plurality of interstitial probes positionable within a volume of tissue, each probe provided with 2 or more electrodes operable to treat the tissue; and a control unit in communication with the probes, the control unit programmed to: deliver energy in bipolar or multipolar mode, or electroporation between 2 or more electrodes to ablate tissue at locations showing high risk of disease, and wherein the current paths are intersecting at a particular location. The electrical energy may be delivered in pulses.

According to some embodiments, the probes with multiple electrodes can be implemented in one of the following methods: a set of hollow conducting tubes of growing diameter, overlapping each other, with isolating material in-between; a flexible electronic circuit, glued to a conventional needle; multi-lumen tube, guiding electrical wiring to the electrodes; or other implementations.

Reference is now made to the figures.

FIG. 1 is an exemplary photograph of a system comprising a plurality of electrodes each electrode in close contact with a volume of tissue in accordance with some embodiments. For example, a plurality of interstitial probes 11, positionable within a volume of tissue 12, each one provided with 2 or more electrodes 15; and a control unit in communication with the probes, the control unit programmed to: deliver electrical current at one or a plurality of frequencies in bipolar or multipolar mode between two or more electrodes sequentially.

In some embodiments, the probes 11 are positioned in the tissue using a template. For example, a perineal template 13 may be used. Optionally, the probes 11 may be inserted into tissue similar to brachytherapy probes. In some embodiments, the system may include a transrectal ultrasound (TRUS) probe 14.

According to some embodiments, the probes may be introduced into the volume of tissue in mostly parallel directions using imaging modalities such as but not limited to: impedance, ultrasound, computed tomography (CT), Magnetic resonance imaging (MRI), positron emission tomography (PET) scan, single-photon emission computerized tomography (SPECT) scan, fluoroscopy, endoscopy, laparoscopy, or any combination or fusion of modalities.

According to some embodiments, the disease may be a tumor. For example: the tissue 12 may be some or the entire prostate gland, or other tissue tumor. The system permits to more accurately discern between tumoral tissue and normal tissue especially determining the boundaries and multifocal foci.

Figure 2:
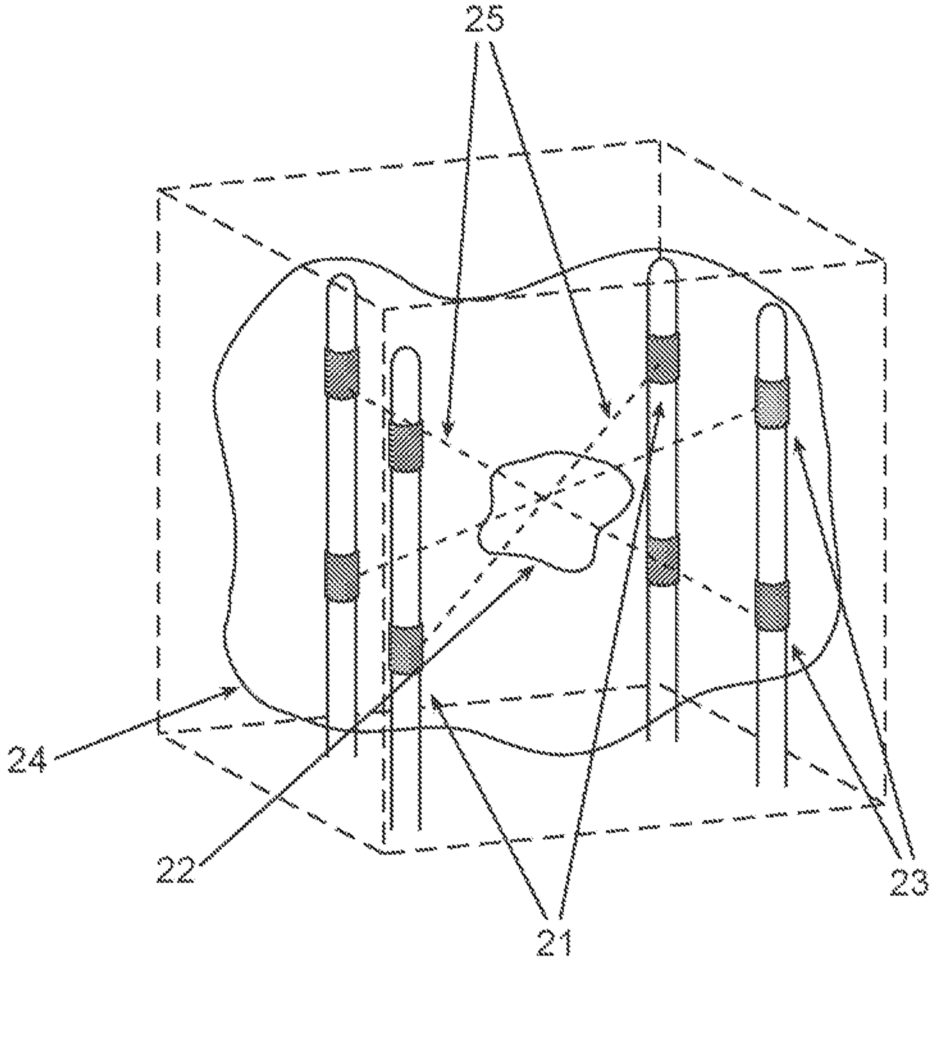
FIG. 2 is a schematic illustration of energy delivered between 2 or more electrodes in accordance with some embodiments of the current invention.

FIG. 2 is a schematic illustration of the ablative electrical energy is delivered between 2 or more electrodes, adjacent one of the plurality of locations in accordance with some embodiments. For example, the ablative electrical energy is delivered between 2 or more electrodes 21, adjacent one of the plurality of locations within a volume of tissue 24 (e.g., a prostate gland). The electrodes 21 optionally include interstitial electrodes.

According to some embodiments, the electrical energy may be delivered in sequential pulses between 2 or more electrodes 21. Optionally, the current paths of the pulses may intersect at a particular location 22 (for example a location of tissue that has been estimated to be diseased). The pulses may have a duty cycle of ½ to 1/25. Optionally, energy may be applied in a way to inhibit heating and/or injury to the tissue adjacent to the electrodes surface 23. Alternatively or additionally, energy may be delivered more evenly in the volume of tissue preventing hot or cold spots. Optionally, the energy may be focused to the intersection of the paths 25.

Figure 3:
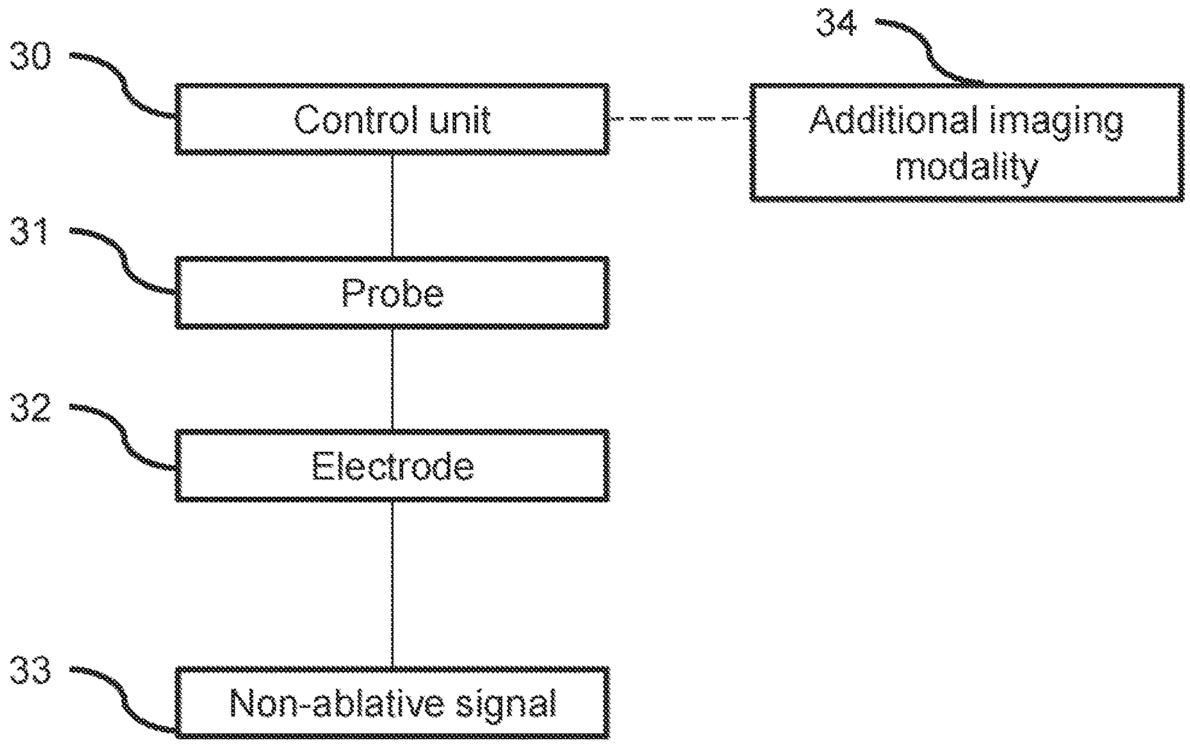
FIG. 3 is a block diagram of evaluation of a tumor in accordance with an embodiment of the current invention.

FIG. 3 is a block diagram of evaluation of a tumor in accordance with an embodiment of the current invention. For example, a control unit 30 in communication with a plurality of interstitial probes 31 configured for positioning a plurality of electrodes 32 within a volume of tissue, wherein the control unit 30 is programmed to deliver energy signals 33 (e.g., non-ablative electrical current) at a plurality of frequencies between various groups of the plurality of electrodes 32, and to calculate a characteristic of the interaction between the signals 33 and the tissue at the plurality of frequencies and at a plurality of locations. Optionally, additional imaging modalities 34 may be combined with the calculated characteristic, for example, to provide an accurate histological map.

Figure 4:
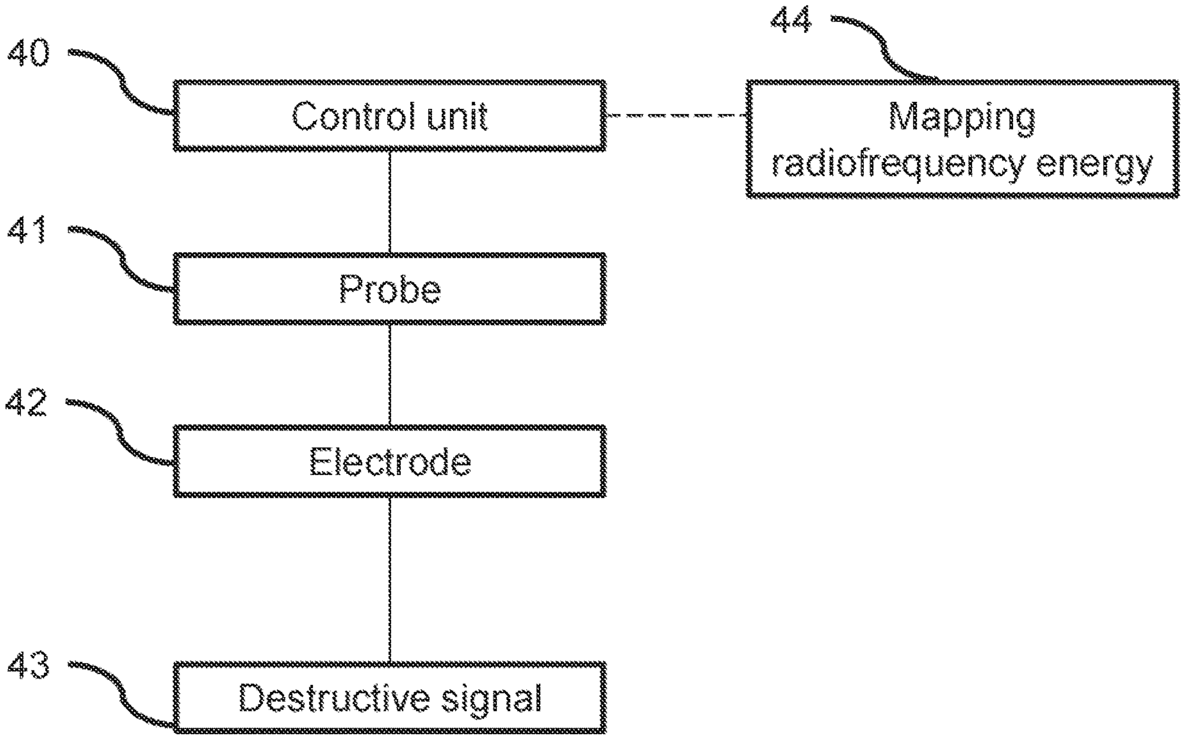
FIG. 4 is a block diagram of treatment of a tumor in accordance with an embodiment of the current invention.

FIG. 4 is a block diagram of treatment of a tumor in accordance with an embodiment of the current invention. For example, a control unit 40 in communication with a plurality of interstitial probes 41 configured for positioning a plurality of electrodes 42 within a volume of tissue, wherein the control unit 40 is programmed to deliver destructive signals 43 (e.g., radiofrequency ablative electrical current at a plurality of frequencies) between various groups of the plurality of electrodes 42 to neutralize (e.g., ablate) target tissue. For example, target tissue may include tissue at locations showing high risk of disease. Optionally, the current paths may be selected to intersect at a particular location (e.g., the target location) causing a therapeutic effect at their intersection and having lesser effect elsewhere. For example, this may inhibit damage to tissue near and/or in contact with the electrodes. Optionally, the therapeutic effect may be delivered to locations with high estimated risk of disease. Optionally, the therapeutic effect may be delivered interstitially at the location of the interstitial probes and/or electrodes. Optionally, mapping non-ablative electrical current 44 may be delivered simultaneously, concomitantly and/or sequentially. Optionally the mapping may be used to plan treatment and/or to monitor the progress of the treatment.

Figure 5:
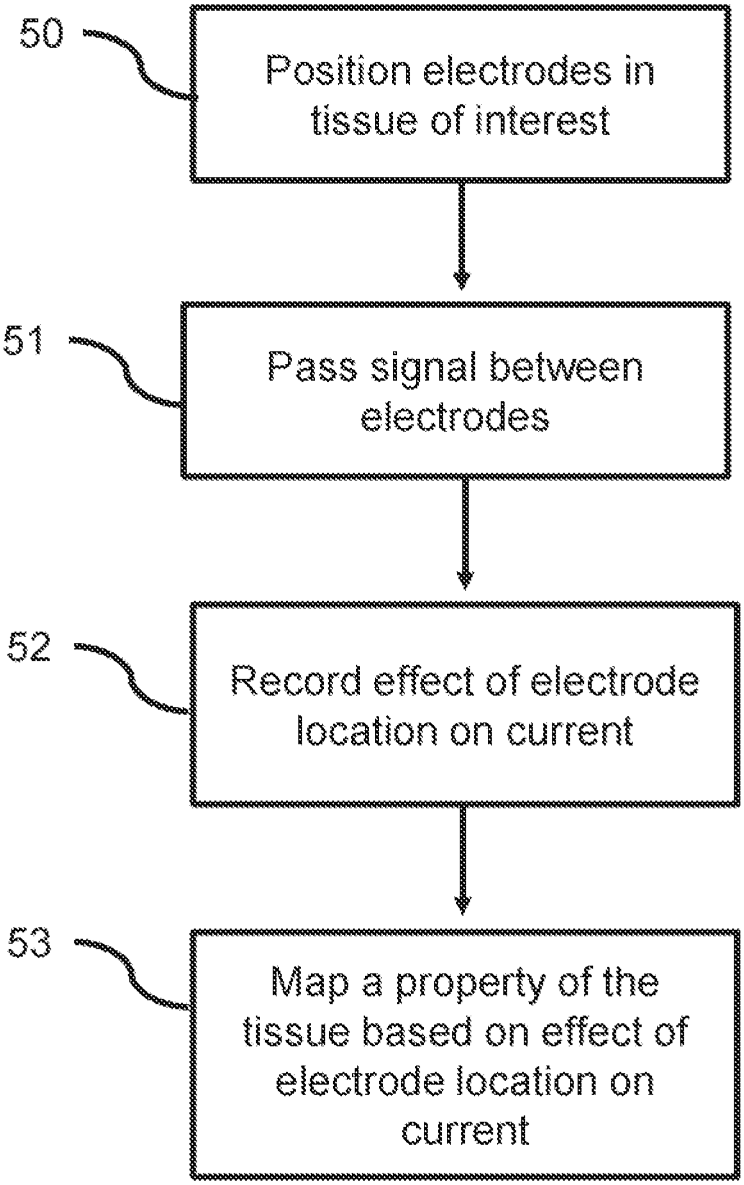
FIG. 5 is a block diagram of evaluation of a tumor in accordance with an embodiment of the current invention.

FIG. 5 is a block diagram of evaluation of a tumor in accordance with an embodiment of the current invention. For example, positioning 50 a plurality of electrodes in tissue of interest, passing 51 electric currents between different groups of the plurality of electrodes, recording 52 an effect of location of the electrodes and/or the signal characteristics on the electrical current, and mapping 53 a property of the tissue based on the effect of the location and type of signals on the electrical current. For example, tomography may be used to map properties of the tissue based on the dependence of the measured currents on the path of the energy in the tissue. Optionally, additional imaging modalities may be combined with the mapped property to provide an accurate histological map. The mapping 53 may be based on multi-dimensional information, for example including 3D tomographic measurement of changes of properties and/or signals in 3D space and/or additional 4-dimensional data including changes of the properties and signals in 3D space over time and/or an additional dimension (for example 4D time based tomographic data dependent on signal frequency and/or additional measurement modalities (e.g., Ultrasound etc.).

In some embodiments, the positioning of trans-perennial probes and/or associated electrodes and/or a measurement probe (e.g., a trans-anal ultrasound probe) may be controlled by a controller using a robot. For example, the robot may control the depth of insertion of multiple trans-perennial probes passing through a template and/or the depth of insertion and/or rotation of the measurement probe. Optionally, the robot may more each probe separately and/or may move an entire array of probes together. The controller may integrate measurements, positioning and treatment.

Figure 6:
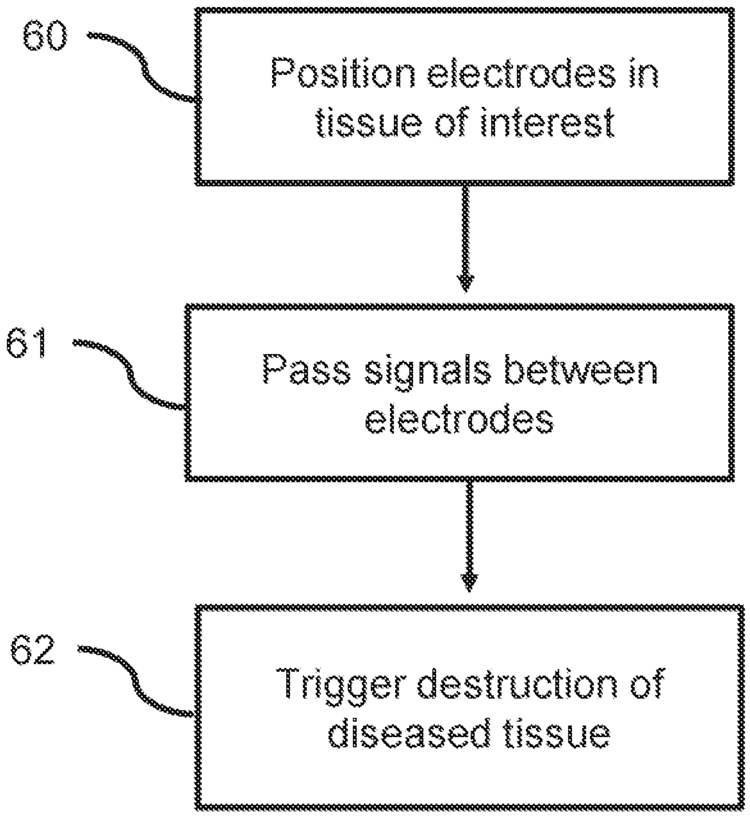
FIG. 6 is a block diagram of treatment of a tumor in accordance with an embodiment of the current invention.

FIG. 6 is a block diagram of treatment of a tumor in accordance with an embodiment of the current invention. For example, positioning 60 a plurality of electrodes in a tissue of interest, passing 61 electric currents between different groups of the plurality of electrodes, and triggering 62 destruction of diseased tissue by the passing, thereby providing a therapeutic effect. Optionally, the passing may be selected from the group including: radiofrequency ablation, electroporation, electrochemical or chemo-electroporation between local pairs of electrodes, or local groups of electrodes.

In a particular embodiment, energy (for example, ablative electrical energy) is delivered in pulses. For example, the ablative energy may induce tissue heating. Alternatively or additionally, the ablative energy may induce electroporation. For example, electroporation maybe performed in monopolar and/or bipolar mode and/or using a low frequency and/or high frequency mode. Pulse duration may be of less than 1 microsecond and/or between 1 to 50 microseconds and/or between 50 to 200 microseconds and/or between 200 microseconds to 3 milliseconds.

In some embodiments, the treatment effect may be monitored using impedance and/or ultrasound and/or doppler ultrasound and/or any combination of the imaging modalities. Additionally or alternatively, a reaction of the tissue to applied energy, chemicals and/or other factors may be used to measure presence of diseased tissue and/or the progress of treatment. For example, where tumor tissue is more sensitive to electroporation than normal tissue, monitoring the change in tissue impedance with initiation of electroporation may assist in refining the tumor risk of each voxel. Optionally, after an initial mapping of the tissue impedance in each voxel, electroporation may be initiated between all, or some pairs of nearby electrodes and/or the change in impedance detected and/or this data may be used to refine the determination of tumor risk in each voxel and/or the progress of treatment.

In some embodiments, the system may be used for any of measurement and/or diagnosis and/or treatments. Optionally, measurement and/or diagnosis and/or treatment may be concurrent. For example, during treatment, changes in impedance and/or recovery of tissue (e.g., stabilization of impedance over time after reversible and/or irreversible electroporation and/or ablation) may be measured over the volume to determine the progress of treatment and/or whether further treatment should be applied to the already treated locations and/or to new locations. Further treatment may be applied based on the new data and/or further measurements made etc. Optionally, during treatment and/or measurement a further probe and/or a probe with more densely positioned electrodes may be added and/or substituted to get a higher resolution measurement and/or treatment of a particular volume of tissue. For example, parallel probes may be positioned at a distance of between 5 to 15 mm and/or between 15 to 30 mm. Optionally, a probe may include multiple electrodes distanced between 1 to 5 mm apart and/or between 5 to 15 mm and/or between 15 to 30 mm. Probes my be inserted one at a time or in groups (e.g., of between 2 to 10 probes and/or between 10 to 30 probes) and/or all the probes of a measurement and/or treatment may be inserted simultaneously.

Optionally, the therapeutic effect may be selected from a group including: contact radiofrequency energy, non-contact radiofrequency energy, electroporation, ultrasonic energy, laser energy, gamma radiation, beta radiation, alpha radiation, immunotherapy, or a combination thereof. Optionally, electrical ablation may induce electroporation. Optionally, electroporation may be delivered in pulses. Optionally, electroporation may be used in conjunction with one or more chemotherapeutic compounds. Optionally, the electroporation used in conjunction with one or more chemotherapeutic compounds may be synergistic. Optionally, the chemotherapeutic may be an anti-cancer compound. Optionally, the anti-cancer compound may be a small molecule, a biological molecule such as an antibody, a metal, an organometallic compound and/or a radio isotope.

General

It is expected that during the life of a patent maturing from this application many relevant building technologies, artificial intelligence methodologies, computer user interfaces, image capture devices, tomography methodologies, electrical diagnosis technologies and/or electrical ablation technologies will be developed and the scope of the terms for design elements, analysis routines, user devices is intended to include all such new technologies a priori.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

The term “impedance” as used herein refers to the ratio of induced voltage to alternating current, presented by the combined effect of resistance and reactance.

The term “impedance tomography” as used herein refers to a noninvasive type of medical imaging in which the electrical conductivity, permittivity, and impedance of a part of the body is inferred from discrete measurements and used to form a tomographic image of that part.

The term “spectroscopy” as used herein refers measurement and interpretation of the electromagnetic spectra that result from the interaction between electromagnetic radiation and matter as a function of the wavelength or frequency of the radiation.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a “circuit,” “module” or “system.” Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are Optionally, provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object-oriented programming language such as Java, Python, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Data and/or program code may be accessed and/or shared over a network, for example the Internet. For example, data may be shared and/or accessed using a social network. A processor may include remote processing capabilities for example available over a network (e.g., the Internet). For example, resources may be accessed via cloud computing. The term "cloud computing" refers to the use of computational resources that are available remotely over a public network, such as the internet, and that may be provided for example at a low cost and/or on an hourly basis. Any virtual or physical computer that is in electronic communication with such a public network could potentially be available as a computational resource. To provide computational resources via the cloud network on a secure basis, computers that access the cloud network may employ standard security encryption protocols such as SSL and PGP, which are well known in the industry.

Some of the methods described herein are generally designed only for use by a computer, and may not be feasible or practical for performing purely manually, by a human expert. A human expert who wanted to manually perform similar tasks might be expected to use completely different methods, e.g., making use of expert knowledge and/or the pattern recognition capabilities of the human brain, which would be vastly more efficient than manually going through the steps of the methods described herein.

As used herein the term "about" refers to ±10%. The terms "comprises", "comprising", "includes", "including", "having" and their conjugates mean "including but not limited to". The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system comprising:

a plurality of electrodes;

a plurality of interstitial probes configured for positioning said plurality of electrodes within a volume of tissue;

each of said plurality of probes provided with at least one of said plurality of electrodes and at least one of said of plurality of probes including a plurality of said electrodes; and a control unit in communication with the probes, the control unit programmed to:

deliver signals at a plurality of frequencies between various groups of said plurality of electrodes; and calculate a characteristic of an interaction between the signals and the tissue at the plurality of frequencies and at a plurality of locations wherein the control unit is further programmed to:

generate a three-dimensional impedance tomography map of the tissue volume based on impedance characteristics measured at the plurality of frequencies between different groups of electrodes;

estimate a disease risk for a plurality of voxels within the tissue volume based on the impedance characteristics; and identify high-risk voxel locations.

2. The system of claim 1, wherein the control unit is configured to control positioning of the plurality of interstitial probes, plurality of electrodes, or both.

3. The system of claim 1, wherein the plurality of interstitial probes is configured to be introduced into the volume of tissue in mostly parallel directions.

4. The system of claim 1, wherein the plurality of interstitial probes is configured to be inserted transperineally.

5. The system of claim 1, wherein the control unit is further configured to perform a comparison between the characteristics detected at each of said plurality of locations.

6. The system of claim 1, wherein the control unit is configured to generate a histological map of the tissue volume depicting a risk of disease at each voxel.

7. The system of claim 1, wherein the control unit is configured to determine impedance magnitude and impedance phase at each of the plurality of frequencies and to separately analyze resistive and reactive impedance components.

8. The system of claim 1, wherein impedance measurements are performed using a tetrapolar configuration in which current is applied through a first set of electrodes and voltage is measured through a second set of electrodes.

9. The system of claim 1, wherein the control unit is configured to deliver ablative electrical energy between selected groups of electrodes such that current paths intersect at selected high-risk voxel locations.

10. The system of claim 1, wherein the control unit is configured to fuse the three-dimensional impedance tomography map with ultrasound imaging data acquired using a transrectal ultrasound probe.

11. The system of claim 10, wherein the control unit is configured to estimate the disease risk for the plurality of voxels based on both the impedance characteristics and the ultrasound imaging data.

* * * * *